US012083222B2

(12) United States Patent
Mehta et al.

(10) Patent No.: US 12,083,222 B2
(45) Date of Patent: Sep. 10, 2024

(54) CHEMOTHERAPEUTIC PHARMACEUTICAL SUSPENSION FOR ORAL DOSAGE

(71) Applicant: ONCOSOL LIMITED, Harrow Middlesex (GB)

(72) Inventors: Sandip Mehta, Ahmedabad (IN); Manish Kumar Umrethia, Ahmedabad (IN); Jayanta Mandal, Ahmedabad (IN)

(73) Assignee: ONCOSOL LIMITED, Harrow Middlesex (GB)

( * ) Notice: Subject to any disclaimer, the term of this patent is extended or adjusted under 35 U.S.C. 154(b) by 469 days.

(21) Appl. No.: 17/265,525

(22) PCT Filed: Aug. 16, 2019

(86) PCT No.: PCT/IB2019/001030
§ 371 (c)(1),
(2) Date: Feb. 3, 2021

(87) PCT Pub. No.: WO2020/039264
PCT Pub. Date: Feb. 27, 2020

(65) Prior Publication Data
US 2023/0255885 A1  Aug. 17, 2023

(30) Foreign Application Priority Data
Aug. 18, 2018 (IN) .............................. 201821030975

(51) Int. Cl.
| | | |
|---|---|---|
| *A61K 9/10* | (2006.01) | |
| *A61K 31/404* | (2006.01) | |
| *A61K 47/02* | (2006.01) | |
| *A61K 47/12* | (2006.01) | |
| *A61K 47/26* | (2006.01) | |
| *A61K 47/36* | (2006.01) | |

(52) U.S. Cl.
CPC ............... *A61K 9/10* (2013.01); *A61K 31/404* (2013.01); *A61K 47/02* (2013.01); *A61K 47/12* (2013.01); *A61K 47/26* (2013.01); *A61K 47/36* (2013.01)

(58) Field of Classification Search
CPC ........ A61K 9/10; A61K 31/404; A61K 47/02; A61K 47/12; A61K 47/26; A61K 47/36; A61K 31/44; A61K 31/506; A61K 31/517; A61K 31/7068; A61K 47/06; A61K 47/38
See application file for complete search history.

(56) References Cited

U.S. PATENT DOCUMENTS

| | | | |
|---|---|---|---|
| 4,788,220 A | 11/1988 | Mody et al. | |
| 5,272,137 A | 12/1993 | Blase et al. | |
| 2007/0208069 A1 | 9/2007 | Krishnan et al. | |
| 2008/0260837 A1 | 10/2008 | Namburi et al. | |
| 2011/0166225 A1 | 7/2011 | Verma et al. | |
| 2014/0276482 A1* | 9/2014 | Astafieva ............... A61K 47/14 | 604/294 |
| 2016/0038612 A1* | 2/2016 | Hoge ................. A61K 48/0075 | 435/173.6 |
| 2016/0089437 A1 | 3/2016 | Hsiao | |
| 2016/0287594 A1 | 10/2016 | Gupta et al. | |
| 2017/0273901 A1* | 9/2017 | Fu ........................... A61P 25/00 | |

FOREIGN PATENT DOCUMENTS

| | | |
|---|---|---|
| EP | 2497467 A1 | 9/2012 |
| IN | 201621039392 A | 5/2018 |
| WO | 2002094220 A1 | 11/2002 |
| WO | 2009082038 A2 | 7/2009 |
| WO | 2018067401 A1 | 4/2018 |
| WO | 2019038584 A1 | 2/2019 |

OTHER PUBLICATIONS

Allen Loyd V Jr: "Zonisamide 10-mg/mL oral suspension", International Journal of Pharmaceutical Compounding, vol. 13, No. 5 Sep. 1, 2009 (Sep. 1, 2009), p. 437, XP009508754,US ISSN: 1092-4221 Retrieved from the Internet: URL:https://www.ijpc.com/Abstracts/Abstract.cfm?ABS=3015 the whole document.

Ferreira Anderson O et al: "Feasibility of amlodipine besylate, chloroquine phosphate, dapsone, phenytoin, pyridoxine hydrochloride, sulfadiazine, sulfasalazine, tetracycline hydrochloride, trimethoprim and zonisamide in SyrSpend SF PH4 oral suspensions", Journal of Pharmaceutical and Biochemical Analysis, vol. 118, Oct. 27, 2015 (Oct. 27, 2015), pp. 105-112, XP029343664, Elsevier B.V, Amsterdam, NLISSN: 0731-7085, DOI:10.1016/J.JPBA.2015.10.032 p. 105-p. 106; table 1.

Anonymous: "SyrSpend-SF: FAQ" FAGRON, Jun. 1, 2016 (Jun. 1, 2016), pp. 1-13, XP055668917, Rotterdam, The Netherlands Retrieved from the Internet: URL:http://fagron.co.za/wp-content/uploads/20160613_SyrSpend-SF_FAQ-for-external_KK_VN_ED_EvT_JC1.pdf, [retrieved on Feb. 14, 2020] the whole document.

DuBois et al., Tolerability and pharmacokinetic profile of a sunitinib powder formulation in pediatric patients with refractory solid tumors: a Children's Oncology Group study; Author manuscript published in Cancer Chemother Pharmacol. (2012) 69(4): 1021-1027.

Paddock Laboratories, Inc., Ora-Plus® Oral Suspending Vehicle, 2010 (2 pp.).

Paddock Laboratories, Inc., Ora-Sweet® Flavored Syrup Vehicle, 2010 (2 pp.).

Navid, et al., Stability of Sunitinib in Oral Suspension; The Annuals of Pharmacotherapy (2008) vol. 42, pp. 962-966.

(Continued)

*Primary Examiner* — Robert A Wax
*Assistant Examiner* — Quanglong N Truong
(74) *Attorney, Agent, or Firm* — Merchant & Gould P.C.; Daniel R. Evans; Daniel J. Pereira

(57) ABSTRACT

Disclosed herein are pharmaceutical compositions in the form of a suspension for oral delivery. Some embodiments provide a pharmaceutical composition in the form of a suspension for oral delivery comprising an anti-cancer active pharmaceutical ingredient; water; a suspending agent; a buffering agent; and one or more of a wetting agent and a binder/filler. In some embodiments, the anti-cancer active pharmaceutical ingredient is selected from ibrutinib, nilotinib, dasatinib, sunitinib, sorafenib, erlotinib, and capecitabine.

20 Claims, No Drawings

(56) References Cited

OTHER PUBLICATIONS

Sistla, et al., Powder-in-Bottle Formulation of SU011248. Enabling Rapid Progression into Human Clinical Trials; Drug Development and Industrial Pharmacy, vol. 30, No. 1, pp. 19-25 (2004).
Pfizer Labs, SUTENT® (sunitinib malate) capsules, for oral use, Prescribing Information 2017 (39 pp.).

* cited by examiner

CHEMOTHERAPEUTIC PHARMACEUTICAL SUSPENSION FOR ORAL DOSAGE

This application is the U.S. national stage application of PCT/IB2019/001030, filed on Aug. 16, 2019, which claims priority to Indian Provisional Application No. IN201821030975 filed on Aug. 18, 2018, which is incorporated herein by reference.

FIELD

This disclosure relates to pharmaceutical compositions in the form of a suspension for oral delivery. Particularly, the suspensions include a suspending agent, a buffering agent and water, in addition to the active pharmaceutical ingredient.

BACKGROUND

Some commercial chemotherapeutics can be dissolved in water, apple Juice, or applesauce for patients having swallowing difficulty but in any treatment an important consideration is to ensure that the patient receives the correct dose of medicine. Administration of tablets by dissolving in this manner may not administer correct and consistent dose every time. Further, many chemotherapeutics have a bitter taste and administration with apple juice may mask its taste and increase the palatability and patient compliance. But apple juice may not be available all the time while administering a drug to the patient. It will therefore be desirable to have dosages in liquid forms which also contain sweeteners and flavors which makes such dosage forms palatable and more patient compliant. Further, liquid dosage forms provide assurance of dosage uniformity upon administration to patients and eliminates difficulty of administration. Liquid dosage forms can also provide physicians more flexibility in designing dosage regimens for patients. Such liquid dosage forms are advantageous to pediatric patients, geriatric patients and those patients who are unable to take oral therapy.

Many active pharmaceutical ingredients are insoluble and are only available in solid dosage forms. This makes it difficult for some patients, such as pediatric or geriatric patients, to take these medications. Formulating such ingredients into a liquid form is often challenging particularly while maintaining dosage requirements, stability and other concerns.

Suspensions are an important class of pharmaceutical dosage forms. The advantages of suspension dosage forms include effective dispensing of hydrophobic drugs; avoidance of the use of co-solvents; masking of unpleasant taste of certain ingredients; offering resistance to degradation of drugs due to hydrolysis, oxidation or microbial activity; easy swallowing for young or elderly patients; and efficient intramuscular depot therapy. In addition, when compared to solution dosage forms, relatively higher concentration of drugs can be incorporated into suspension products. To date, numerous 20 theories have been introduced and successfully used to explain the unique behavior of suspension preparations.

Anticancer drugs represent a very important therapeutic class among others. Anticancer agents are known to have bitter taste and therefore are unacceptable to some patient populations. Further, in many cases, surgery of cancer patients becomes necessary. It is very difficult for such patients who have undergone surgery to swallow oral medicines for few days or weeks. In such a situation, medicine can be administered using a tube. Therefore, if finished dosage form is in liquid, it will be easier to administer dose as compared to any other type of dosage forms.

Many chemotherapeutics are hydrophobic and difficult to disperse which creates handling issues. Handling of chemotherapeutic agents also pose some potential safety concerns for the pharmacy or a compounding pharmacist. Stable liquid compositions as contemplated herein minimize the handling and thus the concern.

Though liquid pharmaceutical compositions of anticancer drugs are advantageous and much more required, they are not much explored by the formulation scientists. Therefore, there is a need existing in the art for the preparation of liquid oral forms of such actives.

SUMMARY

Some embodiments provide a pharmaceutical composition in the form of a suspension for oral delivery comprising an anti-cancer active pharmaceutical ingredient; water; a suspending agent; a buffering agent; and one or more of a wetting agent and a binder/filler.

In some embodiments, the wetting agent is selected from alcohol, glycerin, propylene glycol, polyethylene glycol, mineral oil, benzalkonium chloride, benzethonium chloride, cetylpyridinium chloride, docusate sodium, nonoxynol 9, octoxynol, poloxamer, poloxamer 124, poloxamer 188, 237, 338, 407, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 25 60, polysorbate 80, sodium lauryl sulfate, sorbitan monolaurate, sorbitan monooleate, sorbitan monopalmitate, sorbitan monostearate, tyloxapol, and a combination thereof. In some embodiments, the wetting agent is glycerin.

In some embodiments, the binder/filler is selected from one or more binders or fillers selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof: microcrystalline cellulose, bentonite, colloidal silicon dioxide, microcrystalline cellulose/sodium carboxymethylcellulose, and any combination thereof. In some embodiments, the binder/filler is microcrystalline cellulose/sodium carboxymethylcellulose.

Some embodiments provide a pharmaceutical composition in the form of a suspension for oral delivery comprising an active pharmaceutical ingredient: water; a suspending agent; a buffering agent; and one or more of a wetting agent and a binder/filler. In some instances, the buffering agent is present to yield a pH of about 3 to about 8. In some embodiments, the active pharmaceutical ingredient is an anti-cancer drug. In some embodiments, the anti-cancer drug is selected from ibrtinib, nilotinib, dasatinib, sunitinib, sorafenib, erlotinib, and capecitabine.

In some embodiments, the suspending agent is selected from gelatin, crosslinked polyacrylic acid, polymethacrylic acid, polyhydroxyethyl methacrylic acid, hydroxypropyl methyl cellulose, polyethylene glycol, sodium carboxymethyl cellulose, hyaluronic acid, chitosan, polycarbophil, pectin, copolymers of dextran, polyacrylamide, acacia, copolymer of caprolactone and ethylene oxide, carbopol 934, tragacanth, eudragit, polyvinyl pyrrolidone, polyacrylate and polyacrylate copolymer resins, celluloses and cellulose derivatives for example methyl-, ethyl- and propyl celluloses; hydroxyalkyl-celluloses, hydroxyl propyl celluloses, hydroxylpropylalkyl celluloses and the like including xanthan gum, polyvinyl resins, polyethylene glycol, polyethylene oxide, sorbitol, sucrose, xylitol, dextrose, fructose, maltitol, sugar, sodium alginate, or a combination thereof.

Some embodiments further include one or more binders or fillers selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof, microcrystalline cellulose, bentonite, colloidal silicon dioxide, mycrocrystallin cellulose/sodium carboxymethylcellulose, and any combination thereof.

In some embodiments, the buffering agent is acetate, amino acids, ammonium sulfate, benzoate, bicarbonate, borate, citrate, citric acid monohydrate, disodium hydrogen phosphate, glutamate, lactate, meglumine, potassium citrate, sodium acetate, sodium citrate, sodium phosphate, sulfate, tartrate, triethanolamine, TRIS, trisodium citrate dehydrate, and any combination thereof.

Some embodiments provide a pharmaceutical composition in the form of a suspension for oral delivery comprising an anti-cancer active pharmaceutical ingredient, having poor wettability and log P>2.5; water; a suspending agent; a buffering agent in an amount sufficient to make the composition pH about 4 to about 8; and 300-400 mg/mL wetting agents.

In some embodiments, the wetting agent is selected from alcohol, glycerin, PG, mineral oil, benzalkonium chloride, benzethonium chloride, cetylpyridinium chloride, docusate sodium, nonoxynol 9, octoxynol, poloxamer, poloxamer 124, poloxamer 188, 237, 338, 407, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 25 60, polysorbate 80, sodium lauryl sulfate, sorbitan monolaurate, sorbitan monooleate, sorbitan monopalmitate, sorbitan monostearate, tyloxapol, and a combination thereof. In some embodiments, the wetting agent is glycerin.

In some embodiments, the binder/filler is selected from one or more binders or fillers selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose or an alkali metal salt thereof, microcrystalline cellulose, bentonite, colloidal silicon dioxide, microcrystalline cellulose/sodium carboxymethylcellulose, and any combination thereof. In some embodiments, the binder/filler is microcrystalline cellulose/sodium carboxymethylcellulose.

Some embodiments provide a pharmaceutical composition in the form of a suspension for oral delivery comprising an active pharmaceutical ingredient, having poor wettability and log P>2.5; water; a suspending agent; a buffering agent in an amount sufficient to make the composition pH about 4 to about 8; and 300-400 mg/mL wetting agent. In some embodiments, the active pharmaceutical ingredient is selected from ibrutinib, nilotinib, dasatinib, sunitinib, sorafenib, and erlotinib. Although any suitable suspending agent can be used, in some embodiments, the suspending agent is xanthan gum and HPMC, at about 2 to about 6 mg/mL and about 10 mg/mL, respectively. Although any suitable buffering agent can be used, in some embodiments, the buffering agent is citric acid monohydrate or disodium hydrogen phosphate. Some embodiments further comprise microcrystalline cellulose/sodium carboxymethylcellulose.

In some embodiments, the active pharmaceutical ingredient is selected from dasatinib, sunitinib, sorafenib, and erlotinib; the suspending agent is about 2 to about 10 mg/mL xanthan gum; the buffering agent is citric acid monohydrate or disodium hydrogen phosphate.

Some embodiments provide a pharmaceutical composition in the form of a suspension for oral delivery comprising an active pharmaceutical ingredient, having moderate wettability and log P from about 2 to about 2.5; water; a suspending agent; a buffering agent in an amount sufficient to make the composition pH about 3.5 to about 7; and about 100 mg/mL glycerin. In some embodiments, the active pharmaceutical ingredient is selected from ibrutinib, nilotinib, dasatinib, sunitinib, sorafenib, erlotinib and capecitabine, Although any suitable suspending agent can be used, in some embodiments, the suspending agent is xanthan gum at about 2 to about 3.5 mg/mL. Any suitable buffering agent can be employed, but in some embodiments, the buffering agent is citric acid monohydrate or disodium hydrogen phosphate. In some embodiments, the suspension further comprises microcrystalline cellulose/sodium carboxymethylcellulose.

In some embodiments, the active pharmaceutical ingredient is a suitable chemotherapeutic agent; the suspending agent is about 2 to about 3.5 mg/mL xanthan gum; and the buffering agent is citric acid monohydrate or disodium hydrogen phosphate.

Some embodiments provide a pharmaceutical composition in the form of a suspension for oral delivery comprising an anti-cancer active pharmaceutical ingredient, having good wettability and log P less than about 2; water; a suspending agent; and a buffering agent in an amount sufficient to make the composition pH about 3 to about 8.

In some embodiments, the suspending agent is selected from gelatin, crosslinked polyacrylic acid, polymethacrylic acid, polyhydroxyethyl methacrylic acid, hydroxypropyl methyl cellulose, polyethylene glycol, sodium carboxymethyl cellulose, hyaluronic acid, chitosan, polycarbophil, pectin, copolymers of dextran, polyacrylamide, acacia, copolymer of caprolactone and ethylene oxide, carbopol 934, tragacanth, eudragit, polyvinyl pyrrolidone, polyacrylate and polyacrylate copolymer resins, celluloses and cellulose derivatives for example methyl-, ethyl- and propyl celluloses; hydroxyalkyl-celluloses, hydroxyl propyl celluloses, hydroxylpropylalkyl celluloses and the like including xanthan gum, polyvinyl resins, polyethylene glycol, polyethylene oxide, sorbitol, sucrose, xylitol dextrose, fructose, maltitol, sugar, sodium alginate, or a combination thereof.

Some embodiments provide a pharmaceutical composition in the form of a suspension for oral delivery comprising an active pharmaceutical ingredient, having good wettability and log P less than about 2; water; a suspending agent: and a buffering agent in an amount sufficient to make the composition pH about 3 to about 6. In some embodiments, the suspending agent is xanthan gum at about 3 to about 3.5 mg/mL, although any suitable suspending agent may be used. In some embodiments, the buffering agent is citric acid monohydrate or disodium hydrogen phosphate. Some embodiments further comprise microcrystalline cellulose/sodium carboxymethylcellulose. Some embodiments, depending on the active pharmaceutical ingredient may include up to 25 mg/mL glycerin.

In some embodiments, the suspension comprises an active pharmaceutical ingredient which is a chemotherapeutic agent: a suspending agent which is about 2 to about 3.5 mg/mL xanthan gum; a buffering agent which is citric acid monohydrate or disodium hydrogen phosphate; 0 to 25 mg/mL glycerin; and microcrystalline cellulose/sodium carboxymethylcellulose Some embodiments provide a pharmaceutical composition in the form of a suspension for oral delivery comprising an active pharmaceutical ingredient: water; a suspending agent: a stabilizing amount of glycerin; and a buffering agent in an amount sufficient to make the composition pH about 5 to about 7. In some embodiments, the suspending agent is xanthan gum at about 2 mg/mL. In some embodiments, the buffering agent is citric acid monohydrate or disodium hydrogen phosphate. In some embodiments, the suspension further comprises microcrystalline cellulose/sodium carboxymethylcellulose. In some embodiments, the active pharmaceutical ingredient is capecitabine.

In some embodiments, the suspension comprises a suspending agent which is about 2 mg/mL xanthan gum; a buffering agent which is citric acid monohydrate or disodium hydrogen phosphate; 0 to 25 mg/mL glycerin; and microcrystalline cellulose/sodium carboxymethylcellulose.

Other embodiments will be apparent from this specification without departing from the scope and spirit of this disclosure.

DETAILED DESCRIPTION

Generally, disclosed herein are pharmaceutical compositions in the form of a suspension for oral delivery. Particularly, the suspension includes a suspending agent, a buffering agent and water, in addition to the active pharmaceutical ingredient. Additional excipients may also be used. Glycerin is used as a wetting agent depending on the wettability of the active pharmaceutical ingredient and its log P value. In some instances, glycerin is used in stabilizing amounts rendering the wettability and log P of the active pharmaceutical ingredient is more or less irrelevant. The amount of wetting agent, e.g. glycerin, is generally about 300 mg/mL to about 400 mg/mL for actives with poor wettability and log P>2.5, about 100 mg/mL for actives with moderate wettability and log P between about 2 and about 2.5, and up to about 25 mg/mL for actives with good wettability.

Because of their liquid character, liquid dosage forms represent an ideal dosage form for patients who have difficulty swallowing tablets or capsules. This factor is of particular importance in administration of drugs to children and aged patients. The liquid dosage forms disclosed herein are useful for administering to pediatric and geriatric patients.

Suspensions possess certain advantages over other dosage forms. Some drugs are insoluble in all acceptable media and must, therefore, be administered as a tablet, capsule, or as a suspension. In addition, disagreeable tastes can be masked by a suspension of the drug or a derivative of the drug. Drugs in suspension are chemically more stable than in solution.

The suspensions described herein provide ready to use, suspension dosage forms. Various embodiments describe ready to use, liquid dosage forms in the form of oral suspensions for use with a variety of active pharmaceutical ingredients. In one of the further aspects, liquid dosage forms of the present invention are palatable, oral ready to use formulations (i.e., do not require dilution, mixing with other solvents, or further manipulation of the composition). It may be appreciated that many of the actives have been used in parenteral and solid oral medicinal products, but have not previously been used in oral liquid preparations that were stable over extended periods and that could be retrieved from the packing in a ready to use form as contemplated herein.

The suspensions are room temperature stable, require no reconstitution, and in some embodiments may not even require shaking or mixing just prior to use, which is often required with suspensions.

Suspensions of insoluble drugs may also be used externally, often as protective agents. Drugs in suspension are chemically more stable than in solution. This is particularly important with certain drugs where the pharmacist is often called on to prepare such a suspension just prior to the dispensing of the preparation.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The following terms shall have, for the purposes of this application, the respective meanings set forth below.

"Optional" or "optionally" means that the subsequently described event or circumstance may or may not occur, and that the description includes instances where the event occurs and instances where it does not.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera As a non-limiting example, each range discussed herein can be readily broken down into a lower third, middle third and upper third, et cetera. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

This application discloses a pharmaceutical composition in the form of a suspension for oral delivery comprises an active pharmaceutical ingredient: water: a suspending agent; a buffering agent: and one or more of glycerin and microcrystalline cellulose/sodium carboxymethylcellulose. Generally, the buffering agent will be present in an amount sufficient to achieve a pH of about 3 to about 8.

The Actives. Typically the active pharmaceutical ingredient for use in the suspension disclosed herein are insoluble and thus not well-suited for other liquid dosage forms.

Any suitable anti-cancer or chemotherapeutic active pharmaceutical ingredient may be used. The active pharmaceutical ingredient may be an anti-cancer treatment, such as ibrutinib, nilotinib, dasatinib, sunitinib, sorafenib, erlotinib, or capecitabine. Reference to the active pharmaceutical ingredient also refers to all forms of the active, including a salt thereof, an ester thereof, a free acid form thereof, a free base form thereof, a solvate thereof: a deuterated derivative thereof: a hydrate thereof: an N-oxide thereof, a clathrate thereof: a prodrug thereof, a polymorph thereof, a stereoisomer thereof, an enantiomer thereof, a diastereomer thereof, a racemate thereof, a mixture of stereoisomers thereof, and a combination thereof.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with JAK/STAT modulating compound, can include, but is not limited to, providing an JAX/STAT modulating compound into or onto the target tissue; providing an JAK/STAT modulating compound systemically to a patient by, e.g., intravenous injection whereby the therapeutic reaches the target tissue; providing an JAK/STAT modulating compound in the form of the encoding sequence thereof to the target tissue (e.g., by so-called gene-therapy techniques). "Administering" a composition may be accomplished by injection, topical administration, orally, or by either method in combination with other known techniques.

The term "subject" as used herein includes, but is not limited to, humans and non-human vertebrates such as wild, domestic, and farm animals. In certain embodiments, the subject described herein is an animal. In certain embodiments, the subject is a mammal. In certain embodiments, the subject is a human. In certain embodiments, the subject is a non-human animal. In certain embodiments, the subject is a non-human mammal.

In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The term "improve" is used to convey that the compounds of embodiments herein change either the appearance, form, characteristics and/or the physical attributes of the tissue to which it is being provided, applied or administered. The change in form may be demonstrated by any of the following alone or in combination: enhanced appearance of the skin; at least partial remission, such as repigmentation of existing areas of depigmentation; uniformity of skin color: increased melanin production in white patches; repigmentation of skin; and/or reduced incidence of new areas of depigmentation.

The term "inhibit" includes the administration of a compound of embodiments herein to prevent the onset of the symptoms, alleviating the symptoms, or eliminating the disease, condition or disorder.

By "pharmaceutically acceptable", it is meant the carrier, diluent or excipient must be compatible with the other ingredients of the topical formulation and not deleterious to the recipient thereof.

As used herein, the term "therapeutic" means an agent utilized to treat, combat, inhibit, ameliorate, prevent or improve an unwanted condition or disease of a patient. In part, embodiments of embodiments herein are directed to the treatment of vitiligo.

A "therapeutically effective amount" or "effective amount" of a composition is a predetermined amount calculated to achieve the desired effect, i.e., to induce a favorable immunological response.

Anti-cancer drugs, such as Dasatinib, Sunitinib, Sorafenib, Erlotinib, Capecitabine, and others are particularly well-suited for use in the suspensions described herein. These actives have low solubility and generally are bad tasting, both of which lend themselves to the suspensions disclosed herein.

Wetting Agents. Wetting agents as used herein are routinely used in pharmaceutical formulations, especially in liquid dosage forms to create a homogeneous dispersion of solid particles in a liquid vehicle. This process can be challenging due to a layer of adsorbed air on the particle's surface. Hence, even particles with a high density may float on the surface of the liquid until the air phase is displaced completely. The use of a wetting agent allows removal of adsorbed air and easy penetration of the liquid vehicle into pores of the particle in a short period of time. For an aqueous vehicle, alcohol, glycerin, and PG are frequently used to facilitate the removal of adsorbed air from the surface of particles. Whereas for a non-aqueous liquid vehicle, mineral oil is commonly used as a wetting agent. Additional non-limiting examples of wetting agents are benzalkonium chloride, benzethonium chloride, cetylpyridinium chloride, docusate sodium, nonoxynol 9, octoxynol, poloxamer, poloxamer 124, poloxamer 188, 237, 338, 407, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 25 60, polysorbate 80, sodium lauryl sulfate, sorbitan monolaurate, sorbitan monooleate, sorbitan monopalmitate, sorbitan monostearate, tyloxapol and the like.

Suspending Agents. The viscosity of the suspension may be controlled by the use of one or more suspending agents/thickening agents (or viscosity modifying agents) suitable for pharmaceutical use. These agents ensure that the individual doses removed have constant active ingredient content. The suspending agent may be selected from gelatin, crosslinked polyacrylic acid, polymethacrylic acid, polyhydroxyethyl methacrylic acid, hydroxypropyl methyl cellulose, polyethylene glycol, sodium carboxymethyl cellulose, hyaluronic acid, chitosan, polycarbophil, pectin, copolymers of dextran, polyacrylamide, acacia, copolymer of caprolactone and ethylene oxide, carbopol 934, tragacanth, eudragit, polyvinyl pyrrolidone, polyacrylate and polyacrylate copolymer resins, celluloses and cellulose derivatives for example methyl-, ethyl- and propyl celluloses; hydroxyalkyl-celluloses, hydroxyl propyl celluloses, hydroxylpropyl-alkyl celluloses and the like including xanthan gum, polyvinyl resins, polyethylene glycol, polyethylene oxide, sorbitol, sucrose, xylitol, dextrose, fructose, maltitol, sugar, sodium alginate, or a combination thereof.

In some embodiments, the suspending agent is present in an amount of about 2 mg/mL to about 20 mg/mL, about 2 mg/mL to about 15 mg/mL, about 2 mg/mL to about 10 mg/mL, about 2 mg/mL to about 8 mg/mL, about 2 mg/mL to about 6 mg/mL, about 4 mg/mL to about 20 mg/mL, about 4 mg/mL to about 15 mg/mL, about 4 mg/mL to about 10 mg/mL, about 4 mg/mL to about 8 mg/mL, about 6 mg/mL to about 20 mg/mL, about 6 mg/mL to about 15 mg/mL, about 8 mg/mL to about 20 mg/mL, about 8 mg/mL to about 15 mg/mL and any value within the foregoing range.

Binder/Filler. One or more binders/fillers may be employed in the suspensions described herein. The binders or fillers may be selected from acacia, agar, alginic acid, carmellose sodium, dextrin, veegum or gel white, gellan gum, sodium alginate, hydroxypropyl starch, maltodextrin, modified starch, pectin, potassium alginate, polyvinyl pyrrolidone, carboxymethyl cellulose, microcrystalline cellulose/sodium carboxymethylcellulose or an alkali metal salt thereof, microcrystalline cellulose, bentonite, colloidal silicon dioxide, microcrystalline cellulose/sodium carboxymethylcellulose and any combination thereof.

In some embodiments, the binder/filler is present from about 10 mg/mL to about 25 mg/mL and in some embodiments from 15 mg/mL to 20 mg/mL.

The combination of microcrystalline cellulose/sodium carboxymethylcellulose may be employed as a suspending agent or a dispersing agent, typically in an amount of 15 mg/mL to 20 mg/mL.

Buffering Agent. One or more buffering agents may be employed in an amount sufficient to achieve the desired pH, dependent upon the desired active pharmaceutical ingredient. Suitable buffering agents include acetate, amino acids, ammonium sulfate, benzoate, bicarbonate, borate, citrate, citric acid monohydrate, disodium hydrogen phosphate, glutamate, lactate, meglumine, potassium citrate, sodium acetate, sodium citrate, sodium phosphate, sulfate, tartrate, triethanolamine, TRIS, trisodium citrate dehydrate, and any combination thereof.

As noted above, actives suitable for use in the suspensions disclosed herein are grouped by their wettability and log P or where glycerin is used as a stabilizer.

In some embodiments, the buffering agent is present in an amount sufficient to achieve the desired pH.

For an active pharmaceutical ingredient, having poor wettability and log P>2.5, the pharmaceutical composition in the form of a suspension for oral delivery comprises water; a suspending agent; a buffering agent in an amount sufficient to make the composition pH about 4 to about 8; and 300-400 mg/mL glycerin. Although any suspending agent or agents may be used, in some embodiments, the suspending agent is xanthan gum and HPMC, which are present at about 2 to about 6 mg/mL and about 10 mg/mL, respectively. In some embodiments, the buffering agent is citric acid monohydrate or disodium hydrogen phosphate. Additionally, some embodiments farther include microcrystalline cellulose, typically at about 20 mg/mL.

Thus, in some embodiments, the suspension comprises an active pharmaceutical ingredient; about 2 to about 6 mg/mL xanthan gum and about 10 mg/mL HPMC; a buffering agent selected from citric acid monohydrate or disodium hydrogen phosphate; and (optionally) microcrystalline cellulose/sodium carboxymethylcellulose.

For an active pharmaceutical ingredient, having moderate wettability and log P from about 2 to about 2.5, the pharmaceutical composition in the form of a suspension for oral delivery comprises water; a suspending agent; a buffering agent in an amount sufficient to make the composition pH about 3.5 to about 7; and about 100 mg/mL glycerin.

In particular embodiments, the suspending agent is xanthan gum which is typically present at about 2 to about 3.5 mg/mL. In some embodiments, the buffering agent is citric acid monohydrate or disodium hydrogen phosphate. Microcrystalline cellulose/sodium carboxymethylcellulose may also be present at about 15 mg/mL.

Thus, some embodiments provide a suspension comprising a chemotherapeutic active pharmaceutical ingredient: xanthan gum at about 2 to about 3.5 mg/mL citric acid monohydrate or disodium hydrogen phosphate; and optionally microcrystalline cellulose/sodium carboxymethylcellulose.

For an active pharmaceutical ingredient, having good wettability and log P less than about 2, the pharmaceutical composition in the form of a suspension for oral delivery comprises water: a suspending agent; and a buffering agent in an amount sufficient to make the composition pH about 3 to about 6.

In some embodiments, the suspending agent is xanthan gum typically at about 3 to about 3.5 mg/mL. In some embodiments, the buffering agent is citric acid monohydrate or disodium hydrogen phosphate. As with other suspensions about 20 mg/mL. microcrystalline cellulose/sodium carboxymethylcellulose may be present. Because of the good wettability of the actives in this group, minimal amounts of wetting agent are required. In the case of glycerin up to 25 mg/mL may be used depending on the active. For example, the active zonisamide does not require any glycerin, while primidone formulations use 25 mg/mL.

Thus, some embodiments provide a suspension comprising a chemotherapeutic active pharmaceutical ingredient; xanthan gum as suspending agent at about 2 to about 3.5 mg/mL; citric acid monohydrate or disodium hydrogen phosphate as the buffering agent is: 0 to 25 mg/mL glycerin; and optionally microcrystalline cellulose/sodium carboxymethylcellulose.

Some embodiments employ a stabilizing amount of wetting agent to accommodate a variety of actives. Such pharmaceutical compositions in the form of a suspension for oral delivery comprise an active pharmaceutical ingredient; water; a suspending agent; a stabilizing amount of glycerin; and a buffering agent in an amount sufficient to make the composition pH about 5 to about 7. In some instances, the suspending agent is xanthan gum at about 2 mg/mL. In some instances, the buffering agent is citric acid monohydrate or disodium hydrogen phosphate.

Thus, some embodiments provide a suspension comprising about 2 mg/mL xanthan gum as the suspending agent: citric acid monohydrate or disodium hydrogen phosphate as the buffering agent is; and 0 to 25 mg/mL glycerin.

The active pharmaceutical ingredient may be the anti-cancer drug capecitabine. The suspending agent is xanthan gum at about 2 mg/mL and the buffering agent is sufficient to yield a pH of about 5 to about 7.

Other excipients. The suspension may include addition excipients for various purposes such as flavorants, sweeteners, etc.

Non-limiting examples of flavoring agents are synthetic flavor oils and flavoring aromatics and/or natural oils, extracts from plants leaves, flowers, fruits, and so forth and the like or any combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth and the like or any combinations thereof. Solid forms, such as spray dried forms of flavoring agents, may also be useful in the liquid dosage forms disclosed herein.

Several of the materials classified as sweetening agents are sugar alcohols (also known as polyhydric alcohols, polyols and hydrogenated sugars). Several of the commonly used sweetening agents are ionic and have the potential to interact with other components of the suspension. Some sweetening agents are more stable than others in aqueous solution. These will be important factors in the final selection of the sweetening agent. Non-limiting examples of sweetening agents are Glucose, Sucralose, Trehalose, Fructose, Xylose, Dextrose, Galactose, Tagatose, Maltose, Sucrose, Glycerol, Dulcitol, Mannitol, Lactitol, Sorbitol, Xylitol, Saccharine or the corresponding sodium, potassium or calcium salt, Cyclamate or the corresponding sodium or calcium salt, Aspartame, or Acesulfame or the potassium salt thereof, Dulcin or Ammonium glycyrrhizinate, Alitame, Inulin, Isomalt, Neohesperidin dihydrochalcone, Thaumatin and the like or any combinations thereof.

Other known pharmaceutical excipients may be used in the ordinary amounts for their normal purposes, so long as they do not negatively affect the effectiveness or stability of the suspensions. Examples of additional excipients such as but not limited to fillers/vehicles, solvents/co-solvents, preservatives/antioxidants, suspending agents, surfactants, antifoaming agents, buffering agents, chelating agents, sweeteners, flavoring agents, sweetness/flavor enhancing agents, or combinations thereof will be well-known to those of skill in the art.

Methods of treatment. The suspensions disclosed herein are useful with a variety of active pharmaceutical ingredients to treat a variety of conditions, diseases, disorders, or other ailments. In some embodiments, the suspensions are meant to mimic their solid form counterparts, providing the same effectiveness in the same dose. In each case, the method of treating the condition, disease, disorder or other ailment comprises administering the suspension to a patient in need of such treatment to provide a desired or therapeutically acceptable dose of the active pharmaceutical ingredient.

The methods disclosed are for the treatment of a disease or a condition that can be treated by the active pharmaceutical ingredient in the suspension. The method comprises administering to a patient, such as human, an effective dosage amount of a liquid pharmaceutical composition comprising the active pharmaceutical ingredient and one or more pharmaceutically acceptable excipients or additives as disclosed and described herein.

"Effective dosage amount" as used herein with respect to, for example liquid pharmaceutical compositions of the present invention shall mean that dosage that provides the specific pharmacological response for which the active pharmaceutical ingredient administered in a significant number of subjects in need of such treatment. It is emphasized that "effective dosage amount", administered to a particular subject in a particular instance will not always be effective in treating the diseases described herein, even though such dosage is deemed a "effective dosage amount" by those skilled in the art.

The liquid pharmaceutical compositions of the present invention are proposed to have unexpectedly dramatic dissolution profiles. Rapid dissolution of an administered active agent is preferable, as faster dissolution generally leads to greater bioavailability and faster onset of action. To improve the dissolution profile and bioavailability of the active pharmaceutical ingredient it would be useful to increase dissolution of the active used so that it could attain a level close to 100% dissolution of the drug substance.

The liquid pharmaceutical compositions of the present invention comprising the active pharmaceutical ingredient or salt thereof or derivative thereof, exhibit improved or comparable pharmacokinetic profiles as compared to marketed or known compositions of the same active pharmaceutical ingredient or salt or derivative thereof For example, the Cmax and/or AUC of the liquid pharmaceutical compositions of disclosed herein can be greater than or substantially equal to the Cmax and/or AUC for known or marketed compositions, e.g. solid formulations, administered at the same dose. In addition, the Tmax of the liquid compositions of the present invention can be lower than or substantially equal to that obtained for a known or marketed composition, administered at the same dose. In addition, combinations of an improved or comparable Cmax, AUC and Tmax profile can be exhibited by the liquid compositions of the invention, as compared to known or marketed compositions. In further aspects, the liquid compositions of the present invention may result in minimal different absorption levels when administered under fed as compared to fasting conditions.

The liquid compositions exhibit in comparative pharmacokinetic testing with marketed or known formulations, administered at the same dose, a Tmax not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the Tmax exhibited by the marketed or known formulation.

In some embodiments, the liquid compositions exhibit in comparative pharmacokinetic testing with marketed or known formulation, administered at the same dose, a Cmax which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the Cmax exhibited by the marketed or known formulation.

In one of the further aspects, the liquid compositions of the present invention exhibit in comparative pharmacokinetic testing with marketed or known formulation, administered at the same dose, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least 5 about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the marketed or known formulation.

In some embodiments, the Tmax of the active pharmaceutical ingredient or salt thereof used for the preparation of the liquid composition according to the present invention, when assayed in the plasma of the mammalian subject, is less than about 6 to about 8 hours. In other aspects of the invention, the Tmax of the active pharmaceutical ingredient or salt thereof is less than about 6 hours, less than about 5 hours, less than about 4 hours, less than about 3 hours, less than about 2 hours, less than about 1 hour, or less than about 30 minutes after administration.

In some aspects, the liquid compositions exhibit improved or comparable bioavailability as compared to known or marketed compositions.

The liquid pharmaceutical compositions of the present invention are suitable for use in the industry.

EXAMPLES

Example 1: Poor Wettability, Log P>2.5

A pharmaceutical composition in the form of a suspension for oral delivery comprises an active pharmaceutical ingredient, having poor wettability and log P>2.5; water; a suspending agent; a buffering agent in an amount sufficient to make the composition pH about 4 to about 8; and 300-400 mg/mL glycerin. Exemplary compositions are described below:

| General liquid composition | | |
|---|---|---|
| Sr No | Ingredient | Quantity % w/v |
| 1 | Active pharmaceutical ingredient | 0.01-25% |
| 2 | Suspending agent(s)/thickening agent(s)/viscosity modifying agent(s) | 0.01-10% |
| 3 | Preservative(s) | 0.01-10% |
| 4 | pH adjusting agent(s)/pH modifying agents/Buffering agent(s) | Q.S. to adjust the pH |

-continued

| General liquid composition | | |
|---|---|---|
| Sr No | Ingredient | Quantity % w/v |
| 5 | Solvent(s)/co-solvent(s)/Solubilizer(s) | Q.S. |
| 6 | Anti-foaming agent(s) | 0.01-10% |
| 7 | Surfactant(s) | 0-10% |
| 8 | Stabilizing agent(s)/Anti-oxidant(s) | 0-10% |
| 9 | Wetting agent(s) | 0-10% |
| 10 | Chelating agent(s) | 0-10% |
| 11 | Bulking agent(s)/auxiliary suspending agents | 0-10% |
| 12 | Sweetening agent(s) | 0.01-5% |
| 13 | Flavoring agent(s) | 0.01-5% |
| 14 | Coloring agent(s) | 0-2% |
| 15 | Vehicle(s) | Q.S. |

Q.S. = Quantity Sufficient

Those who are skilled in the art will appreciate that one or more above mentioned excipients can be omitted from the liquid compositions for preparing solutions, say for example suspending agents, bulking agents, anti-foaming agents etc. The above is provided herein for illustration purposes only and should not be construed as the exact or only scope of the present invention.

Particular exemplary formulations are further set forth below:

| Dasatinib oral suspension 40 mg/ml | | | | |
|---|---|---|---|---|
| | | | formula | |
| Sr. No. | Ingredients | Role of Ingredients | % w/v | mg/ml |
| 1 | Dasatinib | Active pharmaceutical ingredient | 4.00 | 40.00 |
| 2 | Methyl parahydroxybenzoate | Preservative | 0.18 | 1.80 |
| 3 | Propyl parahydroxybenzoate | Preservative | 0.02 | 0.20 |
| 4 | Monobasic Sodium phosphate, dihydrate | pH adjusting agent | 0.11 | 1.07 |
| 5 | Dibasic sodium phosphate, dihydrate | pH adjusting agent | 0.06 | 0.56 |
| 6 | Microcrystalline cellulose and carboxymethylcellulose sodium | Suspending agent | 2.00 | 20.00 |
| 7 | Simethicone emulsion 30% | Antifoaming agent | 0.20 | 2.00 |
| 8 | Tween 80 | Wetting agent | 0.20 | 2.00 |
| 9 | Xanthan gum | Suspending agent | 0.30 | 3.00 |
| 10 | Glycerin | Wetting agent | 40.00 | 400.00 |
| 11 | Sucralose powder | Sweetening agent | 0.10 | 1.00 |
| 12 | Peppermint flavour | Flavouring agent | 0.02 | 0.20 |
| 13 | Purified water | Vehicle | Q.S to 100 | Q.S to 1 ml |

Sunitinib Oral Suspension

Some embodiments provide a liquid composition comprising Sunitinib or its pharmaceutically acceptable salts and chemical derivatives such as polymorphs, solvates, hydrates, anhydrous forms, prodrugs, chelates, and complexes thereof and one or more pharmaceutically acceptable excipients selected from the group comprising of vehicles, solvents or co-solvents or solubilizers, suspending agents or thickening agents or viscosity modifying agents, anti-foaming agents, stabilizing agents, anti-oxidants, pH adjusting agents or pH modifying agents or buffering agents, wetting agents, bulking agents or auxiliary suspending agents, chelating agents, surfactants, preservatives, sweetening agents, coloring agents, flavoring agents or combinations thereof. An exemplary composition is shown below:

| Sr. No. | Ingredients | Role of Ingredients | formula % w/v | mg/ml |
|---|---|---|---|---|
| 1 | Sunitinib | Active | 1 | 10 |
| 2 | Sorbitol Solution | Sweetener | 10 | 100 |
| 3 | Microcrystalline cellulose and carboxymethylcellulose sodium | Dispersing agent | 1.5 | 15 |
| 4 | Sodium dihydrogen phosphate, dihydrate | Buffering agent | 0.02 | 0.2 |
| 5 | Dibasic Hydrogen phosphate, dihydrate | Buffering agent | 0.16 | 1.6 |
| 6 | Tween 80 | Wetting agent | 0.20 | 2 |
| 7 | 30% Simethicone emulsion | Antifoaming agent | 0.3 | 3 |
| 8 | Glycerin | Wetting agent | 40 | 400 |
| 9 | Xanthan gum | Viscosity Modifier | 0.2 | 2 |
| 10 | Methyl paraben | Preservative | 0.25 | 2.5 |
| 11 | Ethyl paraben | Preservative | 0.02 | 0.2 |
| 12 | Orange flavor | Flavor | 0.1 | 1 |
| 13 | Purified water | Vehicle | Q. to 100 ml | Q.s to 1 ml |

Sorafenib Oral Suspension

In one of the further aspects, the present invention provides a liquid composition comprising Sorafenib or its pharmaceutically acceptable salts and chemical derivatives such as polymorphs, solvates, hydrates, anhydrous forms, prodrugs, chelates, and complexes thereof and one or more pharmaceutically acceptable excipients selected from the group comprising of vehicles, solvents or co-solvents or solubilizers, suspending agents or thickening agents or viscosity modifying agents, anti-foaming agents, stabilizing agents, anti-oxidants, pH adjusting agents or pH modifying agents or buffering agents, wetting agents, bulking agents or auxiliary suspending agents, chelating agents, surfactants, preservatives, sweetening agents, coloring agents, flavoring agents or combinations thereof. Below is an exemplary composition:

| Sr. No. | Ingredients | Role of Ingredients | formula % w/v | mg/ml |
|---|---|---|---|---|
| 1 | Sorafenib | Active | 8 | 80 |
| 2 | Sucralose | Sweetener | 0.2 | 2 |
| 3 | Microcrystalline cellulose and carboxymethylcellulose sodium | Dispersing agent | 2 | 20 |
| 4 | Citric monohydrate | Buffering agent | 0.372 | 3.72 |
| 5 | Trisodium citrate dihydrate | Buffering agent | 0.4 | 4 |
| 6 | Polysorbate 80 | Wetting agent | 0.15 | 1.5 |
| 7 | 30% Simethicone emulsion | Antifoaming agent | 0.5 | 5 |
| 8 | Glycerin | Wetting agent | 40 | 400 |
| 9 | Xanthan gum | Viscosity Modifier | 0.3 | 3 |
| 10 | Sodium benzoate | Preservative | 0.1 | 1 |
| 11 | Tutti-frutti flavor | Flavor | 0.01 | 0.11 |
| 12 | Purified water | Vehicle | q.s. to 100 ml | q.s to 1 ml |

Erlotinib Oral Suspension 20 mg/ml

In one of the aspects, the present invention provides a liquid composition comprising Erlotinib or its pharmaceutically acceptable salts and chemical derivatives such as polymorphs, solvates, hydrates, anhydrous forms, prodrugs, chelates, and complexes thereof and one or more pharmaceutically acceptable excipients selected from the group comprising of vehicles, solvents or co-solvents or solubilizers, suspending agents or thickening agents or viscosity modifying agents, anti-foaming agents, stabilizing agents, anti-oxidants, pH adjusting agents or pH modifying agents or buffering agents, wetting agents, bulking agents or auxiliary suspending agents, chelating agents, surfactants, preservatives, sweetening agents, coloring agents, flavoring agents or combinations thereof. Below is an exemplary composition:

| Sr. No. | Ingredients | Role of Ingredients | formula % w/v | mg/ml |
|---|---|---|---|---|
| 1 | Erlotinib hydrochloride | Active | 2 | 20 |
| 2 | Sodium benzoate | Preservative | 0.1 | 1.0 |

| Sr. No. | Ingredients | Role of Ingredients | formula % w/v | mg/ml |
|---|---|---|---|---|
| 3 | Citric monohydrate | Buffering agent | 0.62 | 6.2 |
| 4 | Trisodium citrate dihydrate | Buffering agent | 0.88 | 8.8 |
| 5 | Simethicone 30% emulsion | Antifoaming agent | 0.4 | 4.0 |
| 6 | Polysorbate 80 | Wetting agent | 0.2 | 2.0 |
| 7 | Glycerin | Wetting agent | 40 | 400.0 |
| 8 | Xanthan gum | Viscosity Builder | 0.6 | 6.0 |
| 9 | Sucralose | Sweetener | 0.1 | 1.0 |
| 10 | Frozen peppermint flavour 5015241T | Flavoring agent | 0.02 | 0.2 |
| 11 | Water | Vehicle | q.s to 100 ml | q.s to 1 ml |

Those who are skilled in the art will appreciate that different types of liquid pharmaceutical compositions as described herein can be prepared by using suitable excipients or additives known in the art. Thus, the name of excipients or additives and proportionate range thereof provided in the Table-1 is provided herein for the illustration purpose only and should not be construed as the exact or the only scope of the present invention. The liquid pharmaceutical compositions of the present invention may be prepared using suitable excipients or additives in any suitable amount.

Example 2: Glycerin as a Stabilizer

Capecitabine Oral Suspension

In one of the aspects, the present invention provides a liquid composition comprising Capacitabine or its pharmaceutically acceptable salts and chemical derivatives such as polymorphs, solvates, hydrates, anhydrous forms, prodrugs, chelates, and complexes thereof and one or more pharmaceutically acceptable excipients selected from the group comprising of vehicles, solvents or co-solvents or solubilizers, suspending agents or thickening agents or viscosity modifying agents, anti-foaming agents, stabilizing agents, anti-oxidants, pH adjusting agents or pH modifying agents or buffering agents, wetting agents, bulking agents or auxiliary suspending agents, chelating agents, surfactants, preservatives, sweetening agents, coloring agents, flavoring agents or combinations thereof.

| Sr. No. | Ingredients | Role of Ingredients | Prototype Formula % w/v | mg/ml |
|---|---|---|---|---|
| 1 | Capecitabine | Active | 20 | 200 |
| 2 | Xanthan gum | Suspending agent | 0.2 | 2.0 |
| 3 | Methyl 4 hydroxy benzoate | Preservatives | 0.07 | 0.7 |
| 4 | Simethicone 30% emulsion | Anti-foaming agent | 0.5 | 5.0 |
| 5 | Sucralose | Sweetener | 0.2 | 2.0 |
| 6 | Tutti Frutti flavor | Flavoring agent | 0.02 | 0.2 |
| 7 | Glycerin | Stabilizer | 58 | 580.0 |
| 8 | Citric Acid monohydrate | Buffering agent | 0.16 | 1.6 |
| 9 | Tri-Sodium Citrate Di-hydrate | Buffering agent | 0.652 | 6.52 |
| 10 | Water | Vehicle | q.s to 100 ml | q.s to 1 ml |

Impurity Profiles

Stability testing was performed on each of the suspensions as outlined in the tables below. In each instance, the suspension was found to be stable. The liquid dosage form prepared according to the examples above were evaluated for their storage stability under different storage conditions. It was surprisingly found that the liquid dosage forms are stable for prolonged time when tested under different storage conditions. The results of the stability studies conducted are summarized in the table below. These results also show that because of their prolonged storage stability, the liquid dosage forms of the present invention can become a useful alternative to the marketed solid form drugs.

Dasatinib

| Sr. No. | Test | Initial | 40° C. ± 2° C./25% ± 5% RH 3M-(I) | 25° C. ± 2° C./40% ± 5% RH 3M-(I) |
|---|---|---|---|---|
| 1 | Description | Off white colour suspension | Off white colour suspension | Off white colour suspension |
| 2 | pH | 6.52 | 6.44 | 6.52 |
| 3 | Assay of Dasatinib | 97.50% | 98.90% | 92.60% |
| 4 | Content of Methyl paraben | 96.30% | 91.00% | 95.50% |

-continued

| Sr. No. | Test | Initial | 40° C. ± 2° C./25% ± 5% RH 3M-(I) | 25° C. ± 2° C./40% ± 5% RH 3M-(I) |
|---|---|---|---|---|
| 5 | Content of Propyl paraben | 95.00% | 91.00% | 94.10% |
| 6 | Related substances (By HPLC) | | | |
|   | Amino thiazole carboxamide impurity | Not detected | Not detected | Not detected |
|   | N-oxide impurity | Not detected | 0.01% | Not detected |
|   | N-deshydroxyethyl Dasatinib impurity | 0.11% | 0.11% | 0.10% |
|   | Highest individual unspecified impurity | 0.02% (RRT-0.26) | 0.02% (RRT-0.26) | 0.02% (RRT-0.26) |
|   | Total impurities | 0.16% | 0.17% | 0.15% |

Sunitinib

| Test Parameters | Initial | 3M 25/40 | 3M 40/25 |
|---|---|---|---|
| Description | yellowish orange color suspension | yellowish orange color suspension | yellowish orange color suspension |
| Assay of Sunitinib | 97.5% | 98.2% | 100.00% |
| Assay of Methyl Paraben | 85.6% | 84.6% | 57.00% |
| Assay of Ethyl Paraben | 91.8% | 92.0% | 81.90% |
| pH | 7.28 | 7.24 | 7.03 |
| Related Substances | | | |
| Indole-2-one (RRT: −0.72) | 0.01% | 0.01% | 0.01% |
| Desethyl impurity(RRT: 0.94) | 0.05% | 0.06% | 0.07% |
| Carboxamide | ND | ND | ND |
| Single maximum unknown impurity | 0.07% | 0.07% | 0.07% |
| Total impurity | 0.14% | 0.16% | 0.21% |

Sorarenib

| Test Parameters | Initial | 3M 25/40 | 3M 40/25 |
|---|---|---|---|
| Description | Off white suspension. | Off white suspension. | Off white suspension. |
| pH | 4.8 | 4.6 | 4.6 |
| Assay of Sorafenib | 96.0 | 96.00% | 96.40% |
| Content of Sodium Benzoate | 97.9 | 99.40'% | 96.90'% |
| Related Substances by HPLC | | | |
| IMPA | ND | ND | ND |
| IMPB | ND | ND | ND |
| IMPC | ND | ND | ND |
| Single maximum unknown impurity | 0.01% | 0.01% | 0.01% |
| Total impurity | 0.01% | 0.02%, | 0.02% |

Erlotinib

| Test Parameters | Initial | 3M 25/40 6M | 3M 40/25 6M |
|---|---|---|---|
| Description | White to off white suspension | Off white suspension | Off white suspension |
| pH | 4.19 | 4.22 | 4.2 |
| Assay of Erlotinib | 96.5% | 98.5% | 100.7% |
| Assay of Sodium Benzoate | 97.2% | 99.8% | 102.6% |
| Related Substance | | | |
| Impurity-1 | ND | ND | ND |
| Impurity-2 | ND | ND | ND |
| Impurity-3 | ND | ND | ND |
| Impurity-4 | ND | ND | ND |
| Single maximum impurity | 0.05% (RRT-1.08) | 0.07% (RRT-1.09) | 0.08% (RRT-1.08) |
| Total impurities | 0.08% | 0.15% | 0.12% |

Capecitabine

|   |   | Initial | 40/25-3M | 25/40-3M | 25/40-6M | 25/40-9M |
|---|---|---|---|---|---|---|
| 1 | Description | White to offwhite suspension | White to offwhite suspension | White to offwhite suspension | White to offwhite suspension | White to offwhite suspension |
| 2 | Assay of Capecitabine | 103.90% | 98.60% | 109.10% | 101.70% | 104.00% |
| 3 | Assay of Methyl Paraben | 103.30% | 103.50% | 104.30% | 101.80% | 105.60% |
| 4 | Assay of Propyl paraben | 101.00% | 103.10% | 101.30% | 100.10% | 102.50% |
| 5 | pH of Suspension | 5.60 | 5.4 | 5.2 | 5.7 | 5.83 |
| 6 | Related substances (By HPLC) | | | | | |
|   | Imp-A | 0.10% | 3.89% | 0.35% | 0.54% | 0.62% |
|   | Imp-B | 0.04% | 1.62% | 0.23% | 0.49% | 0.55% |
|   | Max. Unspecified Impurity | 0.10% | 0.03% | 0.10% | ND | 0.10% |
|   | Total Impurities | 0.16% | 5.54% | 0.59% | 1.03% | 1.18% |

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Although the present invention has been described in considerable detail with reference to certain preferred embodiments thereof other versions are possible. Therefore, the spirit and scope of the appended claims should not be limited to the description and the preferred versions contained within this specification.

What is claimed is:

1. A pharmaceutical suspension, comprising:
an active pharmaceutical ingredient consisting of sunitinib or a pharmaceutically acceptable salt thereof, in an amount of about 10 mg/mL based on the amount of sunitinib;
about 300 mg/mL to about 400 mg/mL of glycerin;
a suspending agent;
a buffering agent in an amount sufficient to provide a pH of from about 4 to about 8; and
water.

2. The pharmaceutical suspension of claim 1 further comprising a wetting agent selected from alcohol, propylene glycol, mineral oil, benzalkonium chloride, benzethonium chloride, cetylpyridinium chloride, docusate sodium, nonoxynol 9, octoxynol, a poloxamer, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol, and a combination thereof.

3. The pharmaceutical suspension of claim 1, further comprising polysorbate 80.

4. The pharmaceutical suspension of claim 1, wherein the suspending agent comprises xanthan gum in an amount of from about 2 mg/mL to about 6 mg/mL.

5. The pharmaceutical suspension of claim 1, wherein the buffering agent is selected from group consisting of citric acid monohydrate, disodium hydrogen phosphate, sodium dihydrogen phosphate, and a combination thereof.

6. A pharmaceutical suspension, comprising:
an active pharmaceutical ingredient consisting of sunitinib or a pharmaceutically acceptable salt thereof, in an amount of about 10 mg/mL based on the amount of sunitinib;
about 300 mg/mL to about 400 mg/mL of glycerin;
one or more pharmaceutical excipients; and
water.

7. The pharmaceutical suspension of claim 6, wherein the one or more pharmaceutical excipients comprises an antifoaming agent.

8. The pharmaceutical suspension of claim 6, wherein the one or more pharmaceutical excipients comprises an antifoaming agent comprising a simethicone emulsion.

9. The pharmaceutical suspension of claim 6, wherein the one or more pharmaceutical excipients comprises a wetting agent selected from alcohol, propylene glycol, mineral oil, benzalkonium chloride, benzethonium chloride, cetylpyridinium chloride, docusate sodium, nonoxynol 9, octoxynol, a poloxamer, polyoxyl 35 castor oil, polyoxyl 40 hydrogenated castor oil, polyoxyl 10 oleyl ether, polyoxyl 20 cetylstearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol, and a combination thereof.

10. The pharmaceutical suspension of claim 6, wherein the one or more pharmaceutical excipients comprises a wetting agent comprising polysorbate 80.

11. The pharmaceutical suspension of claim 6, wherein the one or more pharmaceutical excipients comprises a wetting agent comprising polysorbate 80 in an amount of about 2 mg/mL.

12. The pharmaceutical suspension of claim 6, wherein the one or more pharmaceutical excipients comprises a preservative comprising methyl paraben, propyl paraben, or a combination thereof.

13. The pharmaceutical suspension of claim 6, wherein the one or more pharmaceutical excipients comprises a buffering agent selected from an amino acid, ammonium sulfate, a benzoate, bicarbonate, borate, citric acid, disodium hydrogen phosphate, lactate, meglumine, a citrate, sodium acetate, sodium citrate, sodium phosphate, sulfate, triethanolamine, TRIS, trisodium citrate dihydrate, or a combination thereof.

14. The pharmaceutical suspension of claim 6, wherein the one or more pharmaceutical excipients comprises a buffering agent selected from citric acid, a citrate, a phosphate, or a combination thereof.

15. The pharmaceutical suspension of claim 6, wherein the one or more pharmaceutical excipients comprises a buffering agent selected from citric acid, a citrate, a phosphate, or a combination thereof in an amount sufficient to provide a pH of from about 4 to about 8.

16. The pharmaceutical suspension of claim 6, wherein the one or more pharmaceutical excipients comprises a gelatin, a crosslinked polyacrylic acid, a polymethacrylic acid, a polyhydroxyethyl methacrylic acid, a polyethylene glycol, a hyaluronic acid, a chitosan, a polycarbophil, a pectin, a copolymer of dextran, a polyacrylamide, an acacia, a copolymer of caprolactone and ethylene oxide, a tragacanth, a polyvinyl pyrrolidone, a polyacrylate, polyacrylate copolymer, a cellulose, a cellulose derivative, a xanthan gum, a polyvinyl resin, a polyethylene oxide, sodium alginate, or a combination thereof.

17. The pharmaceutical suspension of claim 6, wherein the one or more pharmaceutical excipients comprises microcrystalline cellulose, a carboxymethyl cellulose, xanthan gum, or a combination thereof.

18. The pharmaceutical suspension of claim 6, wherein the one or more pharmaceutical excipients comprises xanthan gum.

19. The pharmaceutical suspension of claim 6, wherein the one or more pharmaceutical excipients comprises xanthan gum in an amount of from about 2 mg/mL to about 6 mg/mL.

20. The pharmaceutical suspension of claim 6, wherein the one or more pharmaceutical excipients comprises xanthan gum in an amount of from about 2 mg/mL to about 3 mg/mL.

* * * * *